United States Patent [19]

Kojima et al.

[11] 4,421,746
[45] Dec. 20, 1983

[54] PROCESS FOR PRODUCING INTERFERON INDUCERS

[75] Inventors: Yasuhiko Kojima, Yokohama; Sadao Tamamura; Seishi Konno, both of Tokyo; Takashi Hashimoto, Chofu, all of Japan

[73] Assignee: The Kitasato Institute, Tokyo, Japan

[21] Appl. No.: 392,994

[22] Filed: Jun. 28, 1982

Related U.S. Application Data

[63] Continuation-in-part of Ser. No. 212,065, Dec. 2, 1980, abandoned.

[30] Foreign Application Priority Data

Dec. 3, 1979 [JP] Japan .................................. 54-155627
Dec. 27, 1979 [JP] Japan .................................. 54-170642

[51] Int. Cl.³ ............................................. A61K 35/78
[52] U.S. Cl. .................................................... 424/195
[58] Field of Search .......................................... 424/195

[56] References Cited

U.S. PATENT DOCUMENTS 3,852,423 12/1974 Nakase et al. ...................... 424/115

OTHER PUBLICATIONS

Finter, Interferons and Interferon Inducers pp. 13-17, 139 and 140, North-Holland Pub. Co. 1973.

*Primary Examiner*—Stanley J. Friedman
*Assistant Examiner*—John W. Rollins, Jr.
*Attorney, Agent, or Firm*—Wolder, Gross & Yavner

[57] ABSTRACT

An interferon inducer is produced by extracting a tissue of a plant belonging to the Gound family selected from the group consisting of Benincasa, Cucurbita, Citrullus, Cucumia, Lagenaria, Luffa, Mormordica, Tricsanthes and their variants by water extraction at a temperature of from ambient to the boiling point of the extraction mixture, forming a supernatant from the extracted solution, fractionating the supernatant to yield fractions containing the interferon inducer and recovering same.

27 Claims, No Drawings

PROCESS FOR PRODUCING INTERFERON INDUCERS

RELATED APPLICATION

This application is a continuation-in-part of Ser. No. 212,065 filed Dec. 2, 1980, now abandoned.

BACKGROUND OF THE INVENTION

This invention relates to a process for producing interferon inducers (hereinafter referred to as IF inducers), and more particularly to a process for isolating IF inducers from the tissue or organ of higher plant capable of producing IF inducer. The term "isolating" as used herein denotes concentrating the desired IF inducer and its separation and/or recovery as an effective IF inducer fraction. The term "IF inducer" used herein denotes a substance capable of acting upon the cells of humans or animals to induce interferon (hereinafter referred to as IF). The activity of IF is specific with respect to an animal species and non-specific with respect to a viral species, and may vary, with diferring conditions for its induction. Thus, an IF inducer is of potential interest in the prevention and treatment of humans and animal deceases caused by viral infection, although the active moiety of any IF inducer is not yet clear.

With regard to IF inducers originating from the tissues of higher plants, it was known that certain mitogenic agents such as phytohemagglutinin (PHA), poke weed mitogen and concanavallin A isolated respectively from the plant tissues of kidney bean, poke weed and horse bean, exhibit a very low IF inducing activity. These mitogenic agents are prepared on each occasion, by extracting the tissue with a saline solution or a buffer solution, adding to the extracted solution an alcohol to yield a precipitate containing the active substance, and subjecting the same to column chromatography [J. Biol. Chem. 212, 607–615 (1955); J. Exp. Med., 124:859–872 (1966); and Methods in Carbohydrate Chem., Vol. VI, pages 108–110 (1972)]. Subsequently, Y. Kojima et al [Japanese Patent Application as laid open to public inspection as Kokai Koho No. 32107/78] disclosed an IF inducer isolated from the root of Toki (*Angelica acutiloba* Kitagawa) by extracting the root with hot water, adding to the extracted solution acetone to yield a precipitate and recovering the active substance therefrom. Y. Kojima and S. Tamamura [Japanese Patent Application as laid open to public inspection as Kokai Koho No. 99313/78] disclosed a process for preparing an IF inducer by extracting the peeling of the root of mulberries such as *Morus alba* Linne or *Morus bombycis* Koidz. with hot water, adding an organic solvent to the extracted solution to yield a precipitate and recovering the active substance therefrom. In both cases, the extracted solution may, if desired, be made up to a suitable quantity either by concentration in vacuo or by using a Diaflo membrane.

The present invention is based upon the discovery that high molecular weight fractions which we have isolated from various plants of the family Cucurbitaceae (gourd family) exhibit high IF inducing activity and moreover such active fractions may readily and cheaply be isolated.

An object of the present invention is to provide a process for isolating an IF inducer originating from the tissues or organs of higher plants.

According to the present invention, there is provided a process for isolating high molecular weight fraction having IF inducing activity, by extracting the said IF inducer with water at a temperature of from ambient to the boiling point of the extraction mixture for a period sufficient to extract a substantial portion of the said IF inducer present in the plant tissue, forming a supernatant from the extracted solution, fractionating the supernatant to yield fractions containing a substantial portion of the said IF inducer present in the supernatant and recovering the said IF inducer therefrom. The process of the present invention is characterized by that the plant used is selected from the plants belonging to the gourd family (Cucurbitaceae) capable of producing the said IF inducer and variants thereof.

Various plants of the gourd family are grown in the wild and/or are cultured in various countries of the world. It is said, for example, that in Japan 5 genera and 10 species are grown in the wild and 8 genera and 10 species are cultured for use as foodstuffs or folk cures. These plants include, for example, *Cucumis melo* Linne., *Lagenaris siceraria* Linne and the like. Although any and all plants of Cucurbitaceae (gourd family) may be used for the purpose of the present invention when they are capable of producing the said IF inducer, it is convenient to use plants selected from the genera Benincasa, Cucurbita, Citrullus, Cucumis, Lagenaria, Luffa, Momordica, Tricosanthes and variants capable of producing the said IF inducer. Examples of preferred plants for use are as follows:

| Botanical name | Common name |
| --- | --- |
| *Benincasa hispida* Cogn. syn. *B. cerifera* Saal | Wax gourd (Touga*, Tougan*, Kamouri*) |
| *Cucurbita moschata* Dec. | Pumpkin (Nihon-kabocha*, Tounasu*, |
| *Cucurbita pepo* L. | Somen-kabocha*, Ito-kabocha*, Kinshi-uri* |
| *Cucurbita maxima* Dec. | Kuri-kabocha* |
| *Citrullus vulgaris* Schr. | Water melon |
| *Cucumis melo* L. | Melon |
| *Cucumis sativus* L. | Cucumber |
| *Lagenaria siceraria* Stand. | Gourd (Yugao*, Fukube*, Hyotan*) |
| *Luffa cylindrica* Roem. | Sponge gourd |
| *Momordica charantis* L. | Niga-uri*, Tsuru-reishi* |
| *Tricosanthes cucumeroides* Maxim. | Karasu-uri* |
| *Tricosanthes kirilowii* Maxim. var. *japonica* Kitam. | Kikarasu-uri* |

[*indicates the common name used in Japan]

"An illustrated Flora of the Northern United States, Canada and The British Possessions", Vol. III, pages 290–293 (1943), published by The New York Botanical Garden, New York, N.Y., U.S.A. (hereinafter referred to as Reference 1) indicates that *Cucurbita Pepo* is the type species of the genus Cucurbita. "The Flora of Canada" pages 1432–1433 (1978), published by The National Museum of Canada (hereinafter referred to as Reference 2) indicates the genera Citrullus exemplified by *C. vulgaris* alone, Cucumis exemplified by *C. sativus* alone, and Cucurbita exemplified by *C. pepo* alone. "Flora Europaea", Vol. 2, pages 297–307 (1968), published by Cambridge University Press, Cambridge, UK (hereinafter referred to as Reference 3) indicates that the genus Cucurbita consists of 3 species and that the genus Cucumis consists of 2 species. "Flora of Java", Vol. I, pages 293–307 (1963), published by N. V. P. Noordhoff, Groningen, The Netherland (hereinafter referred as Reference 4) indicates the genera Momordica exemplified by *M. charanti* alone, Luffa consisting of 2 species, Citrullis consisting of one species, Cucumis consisting of 2 species, Benincasa consisting of *B. hispida* alone, Lagenaria consisting of *L. siceraria* alone and Cucurbita consisting of *C. moschata* alone. References 1-4 do not indicate *Tricosanthes kirilowii* and *T. kirilowii* var. *japonica* which are widely found in Japan and China. All plants used for the purpose of the present invention are readily available in Japan. Their harvesting time is generally from mid-summer to autumn.

Although substances having IF inducing activity may be extracted from all tissues or organs of the plant e.g. the stem, root and seed, we have found that the seeds are particularly rich in the IF inducing material. Thus, the following description is made with specific reference to the use of seeds, but it will be appreciated that the extraction of IF inducer from plant tissues or portions other than the seeds falls within the scope of the present invention.

The seed consists of hard hull, thin internal seed coat and cotyledon, and the IF inducer of the present invention is mainly present in the hull and cotyledon. In order to effect the extraction with better efficiency, it is preferred to break the hull prior to extraction. As raw material for extraction, it is preferred to use a dried plant in view of better extraction and preservation, although the fresh plant may, if desired, be used. Although various agents may be used for extraction, the use of water is preferred because it is cheap, readily available and practically applicable. When oils and fats, steroids, pigments and various other impurities (they are in general low molecular weight substances) present in the cotyledon are extracted with a suitbale organic solvent such as for example methanol, ethanol, chloroform, ether, hexane and the like or a mixture threof prior to extraction with water, the purity and yield of the extracted solution may be improved without loss of the active substance which is insoluble in organic solvent. If desired, it is also possible to extract the hull and its ingredients separately. The extraction may be effected with water at any temperature for a period sufficient to extract a major portion of the active material present in the tissue. The ratio of water to the starting plant is convenient (preferably 2-50, e.g. 5-20 times by weight of the plant). Thus, extraction may be effected with hot water for example at 50°-120° C., preferably at 60°-100° C. for 30 minutes to 2 hours when the seeds are extracted. However, a lower temperature e.g. from ambient to 75° C. may be preferred in the case of other tissues than the seeds. Extraction at room temperature for 1-5 days is also possible, if desired, for other tissues than the seeds. Better extraction efficiency may be obtained by adjusting the pH of the extracting solution to an alkaline pH e.g. 7-10 with an alkali e.g. sodium hydroxide, ammonium hydroxide and the like. The extracted solution may contain more or less impurities such as e.g. pigments, low molecular weight substances and the like besides the active substance of the present invention, which may be removed for example by ultrafiltration and/or gel filtration.

It is also possible to treat the extracted solution obtained by using the seeds with phenol. In this case, phenol is added to the aqueous extract to give a concentration of phenol e.g. of 40-55% in the mixture. By heating the mixture for example to 60°-100° C., water and phenol are well mixed to form a uniform liquid phase. This uniform solution is conveniently kept at this temperature for example for 20 minutes to 2 hours and then for example rapidly cooled to a suitable temperature, for example, room temperature so that the water separates from the phenol to give a whitish turbid solution. This solution is allowed to stand, for example, at room temperature or centrifuged (e.g. at 10°-20° C. for 10-30 minutes at 3000-10,000 r.p.m.) so that the solution separates into the water layer and phenol layer. The water layer is rich in the active material. After removal of the water layer, the lower layer i.e. phenol layer is conveniently treated with water in a substantial equal amount to the amount of the removed water. By repeating the above-mentioned heating, rapid cooling and separating treatments, it is possible to recover a major portion of the active material present in the extracted solution (in some cases, more than 90%). The thus-obtained water layers are collected and combined, and the combined water layers are treated in conventional manner (e.g. dialysis, ether extraction and the like) to remove the phenol content. Although it is possible, if desired, to effect extraction with a phenol/water mixture as a first stage, it is preferred to use water in the absence of phenol for ease of operation and economy. However, when compared with treatment using water alone, the phenol treatment may serve to improve the purity of the final product, although the operation may be complicated and expensive. Although the reason for such improvement has not yet been clarified, it is believed that partial purification may be effected by phenol treatment so that various impurities such as proteins may be removed. The purity of the final product obtained by extraction with water is better than the purity of the corresponding final product obtained by phenol treatment, when the crude products are purified by the same procedure.

Instead of the above-mentioned phenol treatment or in combination with it, it may be possible to form a precipitate containing a large amount of the active material, for example (a) by addition of a hydrophilic organic solvent to the extracted solution which may, if desired, be concentrated prior to the addition of the organic solvent, (b) by fractionating the precipitate by the salting out method, or (c) by addition of an alkaline reagent (e.g. Benedict reagent), quaternary ammonium ions, trypaflavine, rivalnol and the like to the extracted solution. However, these treatments are complicated and moreover no additional advantage may be obtained when compared with the extraction with water.

The solution resulting from the extraction with water or from phenol treatment may contain impurities such as e.g. pigments, low molecular weight substances and the like, all having no IF inducing activity, which may if desired be removed by utrafiltration using a semipermeable membrane for fractionating the high molecular weight active fractions. Such a removal may be effected before or after the above-mentioned phenol treatment. However, it is necessary in such a case to remove phenol, ethyl ether and other substances which may injure the ultrafiltration membrane prior to ultrafiltration by any appropriate method, for example, by dialysis, concentration in vacuo and the like.

The active substance obtained by the process of the present invention are water-soluble acidic substances which are imagined to be polysaccharides having a high molecular weight, although their physico-chemical characteristics are not yet clear. When various purified products of the present invention are independently dissolved in water, almost all solutions are able to pass a semi-permeable membrane capable of fractionating substances having a molecular weight of 50,000 calculated as globular protein (e.g. UK-50, commercially available from Toyo Roshi K.K., Tokyo), while some solutions can pass through a ultrafiltration membrane capable of fractinating substances having a molecular weight of 200,000 (as globular protein; e.g. UK-200, commercially available from Toyo Roshi K.K., Tokyo) and other solutions can hardly pass through the same, depending upon the type of plant used as starting material. It is thus important to select the type of the ultrafiltration membrane to be used. Examples of the former are the active materials from the seeds of sponge gourd, gourd and the like, and the latter type are exemplified by the active materials isolated from the seeds of pumpkin, water melon and the like. The fractionation may be effected at a suitable temperature from ambient to the boiling point of the supernatant.

Table 1 shows whether certain active substances obtained from the seeds of various plants of the gourd family are able to pass through certain ultrafiltration membranes, in which "+" indicates that a major portion of the active substances can hardly pass through UK-50 but can pass through UK-200, and "−" indicates that the major portion of the active substances can hardly pass through UK-50 and UK-200 membranes when they are subjected to ultrafiltration effected under normal pressure of 1–5 kg/cm$^2$.

TABLE 1

| Botanical name (Common name) | Permeability |
|---|---|
| *Benicasa hispida* Cogn. syn. *B. cerifera* Saal (Wax gourd) | − |
| *Cucurbita moschata* Dec. (Pumpkin; Nihon-kabocha*) | + |
| *Cucurbita pepo* L. (Kinshi-uri*) | + |
| *Cucurbita maxima* Dec. (Kuri-kabocha*, Pumpkin) | + |
| *Citrullus vulgaris* Schr. (Water melon) | + |
| *Cumis melo* L. (Melon) | − |
| *Cucumis sativus* L. (Cucumber) | − |
| *Lagenaria sicheraria* Stand. (Gourd) | − |

According to another feature of the present invention, there is provided an interferon inducer, which is stable when purified in the form of an amorphous whitish powder and which in substantially pure form possesses the following physico-chemical characteristics:

(1) Molecular weight: at least 30,000;
(2) Melting point or decomposition point: Melting point indefinite. Carbonized at about 220° C.
(3) Ultraviolet absorption spectrum: Maximum absorption at about 258 nm.
(4) Color reaction, obtained by phenol/sulfuric acid reaction: Maximum absorption at about 490 nm.
(5) Solubility in various solvents: Readily soluble in water and aqueous solution of alkali; soluble in saturated aqueous solution of phenol and dimethylsulfoxide; and substantially insoluble in methanol, ethanol, propanol, butanol, acetone, chloroform, diethylether, benzene and hexane.
(6) Reactions: Positive in Molish reaction, chromotropic reaction, tryptophan reaction and orcinol reaction, and negative in diphenylamine reaction.
(7) Nature: Acidic
(8) Main chemical constituents: Phosphoric acid, neutral sugars, uronic acids, and amino compounds.

It is believed that the active substances have in general a molecular weight range of about 30,000 to about 1,000,000 and their IF inducing activity is most prevalent within the range of about 50,000 to about 500,000.

As used in the present specification, the molecular weight of the active materials of the present invention was determined as follows.

The molecular weight ranges of the active materials of the present invention were determined on each occasion by column chromatography using various gel filtration agents such as the series of Sepharose and Sephacryl (commercial products of Pharmacia Fine Chemicals AB., Sweden) and Bio Gel (commercial products of Bio-Rad Laboratories Ltd., U.S.A.). The results were compared with the corresponding results obtained by column chromatography using various reference materials having identified molecular weights such as for example: blue dextran 2000T (*2×10$^6$), $\alpha_2$-macroglobulin from horse serum (*8.2×10$^5$), thyroglobulin from bovine thyroid (*6.69×10$^5$), catalase from bovine lever (*2.1×10$^5$), aldolase from rabbit muscle (*1.58×10$^5$), albumin from bovine serum (*6.7×10$^4$), ovalbumin from hen egg (*4.3×10$^4$), chymotrypsinogen A from bovine panchreas (*2.5×10$^4$), and ribonuclease A from bovine panchreas (*4.3×10$^4$) [*Standard molecular weight].

As the active substances obtained by the process of the present invention are water-soluble acidic high molecular weight substances which are believed to be polysaccharides, it is possible to purify any of the active substances of the present invention by an appropriate method or modification thereof. Such methods for the purification of the substances of this type include, for example, gel filtration, ion exchange chromatography, affinity chromatography, electrophoresis and the like. After this various impurities such as for example salts may, if desired, be removed, for example, by gel filtration, reverse osmosis and various other known methods. Finally, an active substance may be obtained with a high purity by freeze-drying.

The active substances isolated from the seeds of Cucurbitaceae are stable in the form of a whitish amorphous powder and acidic substances which are supposed to be nitrogen-containing polysaccharides. Their molecular weight ranges tend to differ depending upon the type of the starting plant used. When dissolved in water, the solutions are slightly viscous and contain phosphoric acid. The active substances are readily soluble in water, in particular, under alkaline conditions and are also soluble in saturated aqueous solutions of phenol and dimethylsulfoxide, but insoluble in methanol, ethanol, propanol, butanol, ether, acetone, chloroform, benzene and hexane. Decomposition of the active substances of the present invention with dilute sulfuric acid or trifluoroacetic acid yields neutral sugars, uronic acid and amino compounds. Although the sugar compositions and their ratios may vary, depending upon the type of the starting plant used, rhamnose, arabinose, galactose and glucose are neutral sugars common to all active substances. Moreover, at least one of xylose and mannose is found in all active substance, depending upon the type of starting plant used.

The typical example of the uronic acid present in major active substances of the present invention is galacturonic acid which is replaced by glucuronic acid in some cases. The presence of amino sugars is not found. Various ultraviolet absorption spectra obtained by using different plants show generally a maximum absorption at about 258 nm, and the color reaction obtained by the phenol/sulfuric acid method exhibits a maximum absorption at about 490 nm. The active substances are positive in the Molish reaction, chromotropic acid reaction, tryptophan reaction and orcinol reaction, and negative in the diphenylamine reaction. Although their melting point or decomposition points are indefinite, the active substances are carbonized at about 220° C.

As stated above, it is also possible to extract a substance having IF inducing activity from the tissues other than the seeds, i.e. from the stem, leaf and/or root of various plants of the gourd family which are capable of producing the IF inducer and recover the same from the extract thereby obtained in a similar manner to that described above.

Either fresh or dried stems, leaves and/or roots of various plants of Cucurbitaceae may be used for this purpose. Although the physico-chemical properties of the active substances present in the stems, roots and/or leaves are not yet clear, they have lower stability than that of the active materials obtained from the seeds so that their IF inducing activities are substantially inactivated when the extraction is effected, for example, with water at 100° C. for 2 hours. Also, their IF inducing activities are considerably lowered by extraction with a phenol/water mixture. Thus, it is preferred to effect extraction with water at a pH of 7-10 for example for 20 minutes to 2 hours at a temperature of from ambient to 70° C.

The root of the plants of Cucurbitaceae (for example, the roots of the genus Tricosanthes) are long and voluminous and contain a large amount of starch, and thus it is preferred to effect the extraction with water at a temperature which is lower than the gelatinizing temperatures of the starch (e.g. not higher than 60° C.), although it is possible to effect the extraction with a phenol/water mixture at such a relatively low temperature. The physico-chemical characteristics of the active substances obtained from the root are not yet clear, although it is possible to purify the extracted solution in a similar manner to that described above. It has found that the highest activity of the active substances extracted from the roots is capable of passing through an ultrafiltration membrane capable of fractionating substances having a molecular weight, for example, of 30,000 and which is incapable of passing through a cellophane tube used for dialysis. Thus, it is important to select a suitable ultrafiltration membrane, depending upon the types of the starting materials. The extraction time may, for example, be equal to that required for the water extraction from the roots. The activity of the active substances obtained from the roots is, in general, equal to or lower than that of the substances obtained from the seeds. The physico-chemical characteristics of the active substances obtained from the roots are not yet clear. However, the extraction and purification may be effected in a similar manner to that used for extraction from the seeds.

The following non-limiting examples illustrate the invention. In the examples, dried plants were used as starting materials, unless otherwise specified. The IF inducing activities of the products obtained by the process of the present invention were determined by the plaque reduction method. The plant names marked with "*" are the common names employed in Japan.

EXAMPLE 1

Touga* (*Benincasa hispida* Cogn. synonym of *B. cerifera* Saal):

Dried seeds (400 g) of the plant were coarsely crushed and dipped in a mixture of chloroform/methanol (2:1, 1000 ml) for 2 days at room teperature. The dipping was effected twice to remove oils and fats from the seeds, and the solvent was completely removed by evaporation. Water (300 ml) was added to the sample (300 g) which was then heated for one hour in a water bath kept at 90°-100° C. The sample was filtered to give a filtrate. The addition of water (3,000 ml) to the sample, heating, extraction and filtration were repeated three times, and all filtrates were combined. The combined filtrates (8,000 ml) were concentrated under reduced pressure to an amount of 1,100 ml, to which an equal amount of 90% phenol was added, and the combined solutions were kept in a water bath (70°-80° C.) for one hour with occasional agitation. The solution thus obtained possessed a uniform yellowish brown color and was clear. By rapid cooling in a stream of water, a whitish turbid solution was obtained, which was then centrifuged (4,000 r.p.m.) at 10° C. for 20 minutes to separate the water layer (800 ml). Water (800 ml) was added to the lower layer and the mixture was subjected to heating four times, cooling and separation in a similar manner to that described above to give four water layers. Each water layer was treated with diethyl ether (200 ml) and the phenol was removed by extraction with shaking. The ether extraction was effected three times in this manner. All water layers were collected and combined and ether was removed by evaporation. The combined solutions were then subjected to ultrafiltration using an ultrafilter (UHP-76, commercially available from Toyo Roshi K.K., Tokyo) with UK-200 ultrafiltration membrane (commercially available from Toyo Roshi K.K., Tokyo) capable of fractionating substances having a molecular weight of 200,000 to give a residue which was then freeze-dried to obtain a crude power (730 mg). This crude product (300 mg) was dissolved in a tris-HCl buffer solution (pH 8.0; I=0.1; 20 ml) and transferred to a column (26×1,000 mm) packed with Sephacryl S-300 (commercially available from Pharmacia Fine Chemicals AB., Sweden). A similar buffer solution was used for elution. The eluant was divided into fractions (each 5 ml). In accordance with the absorption at 258 nm and with the sugar determined by the phenol/sulfuric acid reaction, the fractions corresponding to the first peak were collected and combined, and the combined fractions were desalted by using an ultrafiltration membrane UH-50 (MW=5,000; commercially available from Toyo Roshi K.K., Tokyo) to give a residue which was then freeze-dried to obtain a final product (100 mg) in the form of a white amorphous powder.

EXAMPLE 2

Nihon-kabocha* (*Cucurbita moschata* Dec.):

The hull (110 g) was treated in a similar manner to that described in Example 1 except that the fractions capable of passing through an ultrafiltration membrane YK-200 (capable of fractionating substances having a molecular weight of 200,000) and incapable of passing through an ultrafiltration membrane UK-50 (capable of fractionating substances having a molecular weight of 50,000) were collected and combined, and the combined fractions were freeze-dried to give a crude product (530 mg), 100 mg of which was transferred to a column (26×400 mm) packed with Ecteola cellulose (commercially available from Serva Entwicklungslabor, W-Germany) treated with a similar tris-HCl buffer solution to that described in Example 1. The elution was effected in a similar manner to that described in Example 1. After no sugar was observed, a further elution was effected by using a similar buffer solution together with 0.3 M sodium chloride (200 ml). The eluant was treated in a similar manner to that described in Example 1 to obtain a final product (20 mg) in the form of a white amorphous powder.

EXAMPLE 3

Nihon-kabocha* (*Cucurbita moschata* Dec.)

The cotyledon (95 g) of the title plant was extracted with hot water in a similar manner to that described in Example 1, the filtrate being treated with phenol and 500 mls of water being used on each occasion. The solutions obtained were then subjected to ultrafiltration in a similar manner to that described in Example 2 to obtain a crude product (85 mg) which was transferred to a column (25×400 mm) packed with Bio-Gel 200 (commercially available from Bio-Rad Laboratories Ltd., U.S.A.) and treated in a similar manner to that described in Example 1 to yield a white amorphous solid (15 mg).

EXAMPLE 4

Somen-kabocha* (*Cucurbita pepo* L.)

The seeds (30 g) were treated in a similar manner to that described in Example 1 to obtain a crude product (95 mg), 90 mg of which were treated in a similar manner to that described in Example 3 to obtain a white amorphous solid (18 mg).

EXAMPLE 5

Kuri-kabocha* (*Cucurbita maxima* Dec.)

The seeds (200 g) were crushed coarsely and defatted, extracted and treated with phenol in a similar manner to that described in Example 1 and subjected to ultrafiltration in a similar manner to that described in Example 2 to obtain a crude product (615 mg), 300 mg of which were transferred to a column (26×1000 mm) packed with DEAE Sephadex A-25 (commercially available from Pharmacia Fine Chemicals AB., Sweden) and treated in a similar manner to that described in Example 2 to yield a white amorphous solid (43 mg).

EXAMPLE 6

Suika* (*Citrullus vulgaris* Schr.)

The seeds (30 g) were treated in a similar manner to that described in Example 1 to obtain a crude product (45 mg) which was transferred to a column (16×1000 mm) packed with DEAE Sephadex A-25 and treated in a similar manner to that described in Example 2 to yield a white amorphous solid (10 mg).

EXAMPLE 7

Melon (*Cucumis melo* L.)

The fresh seeds (60 g) of Honey Dew melon from U.S.A. were treated in a similar manner to that described in Example 1 to obtain a crude product (103 mg), 100 mg of which were treated in a similar manner to that described in Example 3 to yield a white amorphous solid (15 mg).

EXAMPLE 8

Ki-uri* (*Cucumis sativus* L.)

The seeds (50 g) of Shimotsuki Aonaga (trade name) Ki-uri were treated in a similar manner to that described in Example 1 to obtain a crude product (140 mg) which were treated in a similar manner to that described in Example 2 except that DEAE Sephadex A-25 was used instead of Ecteola cellulose to yield a whitish amorphous solid (30 mg).

EXAMPLE 9

Yugao* (*Lagenaria siceraria* Stand.)

The seeds of Sakigake (trade name) Yugao (100 g) were treated in a similar manner to that described in Example 1 to obtain a crude product (125 mg), 100 mg of which were treated in a similar manner to that described in Example 1 to yield a whitish amorphous solid (35 mg).

EXAMPLE 10

Hechima* (*Luffa cylindrica* Roem.)

The seeds of Onaga (trade name) Hechima (100 g) were treated in a similar manner to that described in Example 1 to obtain a crude product (110 mg), 100 mg of which were treated in a similar manner to that described in Example 1 to yield a whitish amorphous solid (25 mg).

EXAMPLE 11

Niga-uri* (*Momordica charantis* Linne)

The seeds of Onaga Nishaku Niga-uri (trade name) (40 g) were treated in a similar manner to that described in Example 1 to obtain a crude product (147 mg), 100 mg of which were treated in a similar manner to that described in Example 1 to yield a whitish amorphous solid (22 mg).

EXAMPLE 12

Karasu-uri* (*Tricosanthes cucumeroids* Maxim.)

The hulls (100 g) were treated in a similar manner to that described in Example 1 to obtain a crude product (200 mg), 100 mg of which were treated in a similar manner to that described in Example 1 to yield a whitish amorphous solid (35 mg).

EXAMPLE 13

Kikarasu-uri* (*Tricosanthes kirilowii* Maxim.)

In a similar manner to that described in Example 1, the hulls were defatted and the defatted hulls (56 g) were processed to obtain a crude product (150 mg), 140 mg of which were transferred to a column (26×400 mm) packed with Sephadex G-200 (commercially available from Pharmacia Fine Chemicals AB., Sweden). Subsequent processing was conducted in a similar manner to that described in Example 1 to yield a whitish amorphous solid (25 mg).

EXAMPLE 14

Kikarasu-uri* (*Tricosanthes kirilowii* Maxim. var. *japonica* Kitam.)

In a similar manner to that described in Example 1, the cotyledon was defatted and the defatted sample (36 g) was processed to obtain a crude product (120 mg), 100 mg of which was treated in a similar manner to that described in Example 3 to yield a whitish amorpgous solid (20 mg).

EXAMPLE 15

*Cucumis sativus* L. (Cucumber)

The stems (40 g) was cut into small pieces and dipped in water (600 ml) at 65° C. for 2 hours. The extracted solution was filtered to remove solids which were then washed with water (200 ml). The filtrate was combined with the washing liquid and the combined solutions (550 ml) were subjected to ultrafiltration using an ultrafiltration membrane (YM-30, commercially available from Amicon Corpn., U.S.A.) capable of fractionating substances having a molecular weight of 30,000 at a pressure of 2 kg/cm². The fractions passing through the membrane were removed and the residue was freeze-dried to give a crude product (480 mg), 400 mg of which were treated in a similar manner to that described in Example 1 to yield an off-white solid (52 mg).

EXAMPLE 16

*Tricosanthes kirilowii* Maxim. var. *japonica* Kitam.

The roots were crushed and 100 g of the crushed roots were dipped in water (400 ml) at room temperature overnight. After this, 90% phenol (400 ml) was added to the extracted solution which was heated at 70°–80° C. for one hour. After cooling, the white turbid phase was collected and centrifuged (3000 r.p.m.; 20 minutes) to obtain a clear liquid phase (100 ml). The remaining phenol phase was treated with water (100 ml) and the mixture added to the residue resulting from the filtration. In this manner, the heating, cooling and separation were repeated four times, resulting in a water phase of 565 ml in total. This phase was subjected to ultrafiltration using an ultrafiltration membrane capable of of fractionating substances having a molecular weight of 50,000 (UK-50, commercially available from Toyo Roshi K.K., Tokyo) to give a filtrate which was concentrated in vacuo and freeze-dried to yield an off-white solid (75 mg).

Experiment 1

IF induction with IF inducer and IF assay: [Reference: Y. Kojima's report in Kitasato Arch. Exp. Med., 43:35 (1970)]

(a) IF induction in vitro:

A rabbit (weight about 1 kg; New Zealand White; SPF) was sacrificed by cardic puncture and its spleen, bone marrow and lymph node cells were collected and mixed together to prepare a cell suspension ($10^7$ cells/ml) which was divided into fractions (each 1 ml). The sample were independently added with 10, 1.0 and 0.1 µg/ml of the final product prepared by the method of the example. The mixture was cultured at 25° C. for 24 hours, followed by centrifugation (9000 r.p.m. for 20 minutes) to form supernatants, each of which was used to determine the IF activity induced.

(b) IF induction in vivo:

An IF inducer obtained in a similar manner to that described in the example was dissolved in water (500 µg/ml) and injected into the auticular vein of a rabbit (weight about 1 kg; New Zealand White; SPF). 1, 2, 4 and 6 hours after administration, a 2 ml sample of blood was removed on each occasion from the test animal and the serum of each sample was isolated from the blood and was used as a sample for determining the activity of the IF induced in the serum.

(c) Determination of IF activity induced:

In both methods (a) and (b), Vesicular stomatitis virus was used as the challenge virus in order to determine the activity of the IF induced by the plaque reduction method. A monolayer culture of the lined cells of RK-13 of rabbit was put in a dish, to which a predetermined amount of the solution obtained by the above-mentioned (a) or (b). The culture was incubated at 37° C. overnight. Then Vesicular stomatitis virus was added to the culture and the incubation was effected at 37° C. overnoght. The IF activity induced was determined and the unit of the IF activity was expressed by the reciprocal number of the highest dilution of the sample required for reducing the number of plaques to 50%.

The plaque reduction method is widely recognized as one of the standard methods for assaying the activity of IF induced with reference, for example, to U.S. Pat. Nos. 4,049,794 and 4,079,126; N. B. Finter, Interferons and Interferon Inducers, pages 139–140 (1973) and William Stewart II, Interferon System, page 15 (1979). This method is also used for this purpose, for example, in U.S. Pat. Nos. 3,719,754; 3,800,035; 3,852,423; 4,027,021; 4,079,552; and 4,124,702. In U.S. Pat. No. 4,079,126, the determination of the activity of the IF induced is effected by the method of Kojima et al i.e. the plaque reduction method disclosed e.g. in Kojima's report in Kitasato Arch. Exp. Med., 43:35 (1970) which is referred to in the present experiment.

Experiment 2

Identification of any IF inducer:

All samples prepared by the above-described examples were respectively treated by the methods of Experiment 1. On each occasion, it has been confirmed that the sample treated by the method of (a) or (b) inhibits the growth of Vesicular stomatitis virus and Vaccinia virus in RK-13 lined cells obtained from rabbit, while does not inhibit the growth of Vaccinia virus or Vesicular stomatitis virus in L cells of mice of the different animal species from rabbit. Moreover, their IF activities induced are inactivated when treated with trypsin at 37° C. for 2 hours. These facts indicate that the active materials prepared by the process of the present invention represent IF inducers which are in conformity with the widely recognized definition of any IF inducer.

Experiment 3

IF activities induced in vitro or in vivo:

The results obtained from the experiments carried out by the methods of Experiment 1 using the samples prepared by the process of the present invention are shown in the following tables.

TABLE 1

| Botanical name (Common name) (*-Japanese common name) | (in vitro) Concentration of sample (µg/ml) | | | |
|---|---|---|---|---|
| | 10. | 1. | 0.1 | 0.01 |
| | IF Activity | | | |
| *Benincasa hispida* Cogn. (Touga*, Wax gourd) | >100 | >100 | 70 | 30 |
| *Cucurbita moschata* Dec. (Nihon-kabocha*, pumpkin) | >100 | >100 | >100 | 70 |
| *Cucurbita pepo* L. (Somen-kabocha*) | >100 | >100 | >100 | 50 |
| *Cucurbita maxima* Dec. (Kuri-kabocha*) | >100 | >100 | >100 | >100 |
| *Citrullus vulgaris* Schr. (Water melon, Suika*) | >100 | 90 | 40 | <10 |
| *Cucumis melo* L. (Melon) | >100 | 50 | 10 | <10 |
| *Cucumis sativus* L. (Cucumber) | 90 | 70 | 30 | <10 |

TABLE 1-continued (in vitro)

| Botanical name (Common name) (*-Japanese common name) | Concentration of sample (μg/ml) | | | |
|---|---|---|---|---|
| | 10. | 1. | 0.1 | 0.01 |
| | IF Activity | | | |
| *Lagenaria siceraria* Stand. (Gourd) | >100 | >100 | 80 | 40 |
| *Luffa cylindrica* Roem. (Sponge gourd) | >100 | 90 | 50 | <10 |
| *Momordica charantis* L. (Niga-uri*) | 80 | 30 | 10 | <10 |
| *Tricosanthes cucumeroides* Maxim. (Karasu-uri*) | >100 | 40 | 20 | <10 |
| *Tricosanthes kirilowii* Maxim. var. *japonica* Kitam. (Kikarasu-uri*) | >100 | 60 | 30 | <10 |
| *Cucumis sativus* L. (stem)** | >80 | 40 | <10 | <10 |
| *Tricosanthes kirilowii* (root) Maxim. var. *japonica* Kitam.** (root) | >100 | 50 | 20 | <10 |

[Note:
Seeds were used in each case except where marked **]

TABLE 2

(in vivo)

| Example No. | Botanical name (common name)* | IF activity in the serum (1mg/rabbit)** |
|---|---|---|
| 1 | *Benincasa hispida* Cogn. (Touga*, wax gourd) | 150 ± 25% |
| 2 & 3 | *Cucurbita moschata* Dec. (Nihon-kabocha*, pumpkin) | 200 ± 20% |
| 4 | *Cucurbita pepo* L. (Somen kabocha*) | 180 ± 25% |
| 5 | *Cucurbita maxima* Dec. (Kuri-kabocha*) | 300 ± 45% |
| 6 | *Citrullus vulgaris* Schr. (Water melon) | 130 ± 45% |
| 7 | *Cucumis melo* L. (Melon) | 50 ± 15% |
| 8 | *Cucumis sativus* L. (Cucumber) | 95 ± 25% |
| 9 | *Lagenaria siceraria* Stand. (Gourd) | 180 ± 30% |
| 10 | *Luffa cylindrica* Roem. (Sponge gourd) | 120 ± 20% |
| 11 | *Mormordica charantis* L. (Niga-uri*) | 40 ± 12% |
| 12 | *Tricosanthes cucumeroides* Maxim. (Karasu-uri*) | 120 ± 20% |
| 13 & 14 | *Tricosanthes kirilowii* Maxim. var. *japonica* Kitam. (Kikarasu-uri*) | 140 ± 30% |
| 15 | *Cucumis sativus* L. (stem)# | 120 ± 25% |
| 16 | *Tricosanthes kirilowii* Maxim. var. *japonica* Kitam. (root)# | 170 ± 30% |

Notes:
*Common name in Japan.
**Mean value, 2 hours after administration to 2 rabbits.
All samples used the seeds except those marked with #.

We claim:

1. A process for producing water-soluble interferon inducer, which comprises extracting with water the tissue of a plant belonging to the Gourd family and selected from the genera group consisting of Benincasa, Cucurbita, Citrullus, Cucumis, Lagenaria, Luffa, Mormordica, Tricosanthes and their variants capable of producing the said interferon inducer, at a temperature of from ambient to the boiling point of the extraction mixture, conducting the extraction for a period sufficient to extract the major portion of the said interferon inducer present in the said tissue, forming a supernatant from the extracted solution thus obtained, fractionating the supernatant to yield fractions containing the major portion of the said interferon inducer present in the supernatant, and recovering said interferon inducer therefrom.

2. The process of claim 1, wherein the plant is one belonging to the genus Benincasa.

3. The process of claim 2, wherein the plant is Benincasa hispida.

4. The process of claim 1, wherein the plant is one belonging to the genus Cucurbita.

5. The process of claim 4, wherein the plant is selected from *Cucurbita moschata, Curcurbita pepo* and *Curcurbita maxima*.

6. The process of claim 1, wherein the plant is one belonging to the genus Citrullus.

7. The process of claim 6, wherein the plant is *Circullus vulgaris*.

8. The process of claim 1, wherein the plant is one belonging to the genus Cucumis.

9. The process of claim 8, wherein the plant is selected from *Cucumis melo* and *Cucumis sativus*.

10. The process of claim 1, wherein the plant is one belonging to the genus Langenaria.

11. The process of claim 10, wherein the plant is *Lagenaria siceraria*.

12. The process of claim 1, wherein the plant is one belonging to the genus Luffa.

13. The process of claim 12, wherein the plant is *Luffa cylindrica*.

14. The process of claim 1, wherein the plant is one belonging to the genus Mormordica.

15. The process of claim 14, wherein the plant is *Mormordica charantis*.

16. The process of claim 1, wherein the plant is one belonging to the genus Tricosanthes.

17. The process of claim 16, wherein the plant is selected from *Tricosanthes cucumeroides* and *Tricosanthes kirilowii* var. *japonica*.

18. The process of claim 1, wherein the water soluble high molecular weight fraction has a molecular weight of from about 30,000 to about 1,000,000.

19. The process of claim 18, wherein the plant tissue is the seed.

20. The process of claim 1, wherein the extraction is effected under alkaline conditions.

21. The process of claim 20, wherein the extraction is effected at a pH of from 7 to 10.

22. The process of claim 1, wherein the extraction is effected at a temperature of from 50° to 120° C. for 30 minutes to 120 minutes.

23. The process of claim 1, further comprising the steps adding phenol to the supernatant at a concentration of 40–55% to form a water/phenol mixture, heating the mixture at 60°–100° C. for 20 to 120 minutes, cooling the mixture for a period sufficient to separate from the phenol layer the water layer as a function containing a major portion of the said interferon inducer present in the supernatant.

24. A process for isolating a water-soluble high molecular weight fraction having a molecular weight range of from about 50,000 to about 1,000,000 active as an interferon inducer, which comprises extracting with water a plant belonging to the Gourd family selected from the group consisting of Benincasa, Cucurbita, Citrullus, Cucumis, Lagenaria, Luffa, Mormordica, and Tricosanthes and their interferon inducer-producing variants, said water being at a temperature of from ambient to the boiling point of the extraction mixture, conducting said extraction for a period sufficient to extract a major portion of said interferon inducer present in the plant tissue, forming a supernatant from the extracted solution, subjecting the said supernatant to ultrafiltration by using an ultrafiltration membrane capable of fractionating substances having a molecular weight of more than 50,000 thereby recovering said interferon inducer.

25. The process of claim 24, wherein the ultrafiltration is effected to fractionate substances having a molecular weight of more than 200,000.

26. The process of claim 24, wherein the extraction is conducted at a temperature of 60° to 100° C. for 30 to 120 minutes.

27. The process of claim 24, wherein the extraction is conducted for 1 to 7 days at room temperature.

* * * * *